(12) United States Patent
Kobayashi

(10) Patent No.: US 6,352,954 B1
(45) Date of Patent: Mar. 5, 2002

(54) MICROENCAPSULATED LEWIS ACID

(75) Inventor: Shu Kobayashi, Tokyo (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/622,196

(22) PCT Filed: Feb. 12, 1999

(86) PCT No.: PCT/JP99/00626

§ 371 Date: Sep. 25, 2000

§ 102(e) Date: Sep. 25, 2000

(87) PCT Pub. No.: WO99/41259

PCT Pub. Date: Aug. 19, 1999

(30) Foreign Application Priority Data

Feb. 13, 1998 (JP) .......................... 10-031880

(51) Int. Cl.⁷ ..................... B01J 31/00; B01J 23/00; B32B 15/02; B32B 17/02; B32B 17/10

(52) U.S. Cl. ................ 502/159; 502/152; 502/168; 502/302; 428/402.2; 428/402.21; 428/402.24; 428/403; 428/417

(58) Field of Search .................. 502/159, 152, 502/168, 302; 428/402.2, 402.21, 402.24, 403, 417

(56) References Cited

U.S. PATENT DOCUMENTS

| | | | | |
|---|---|---|---|---|
| 4,138,362 A | * | 2/1979 | Vassiliades et al. | .......... 252/516 |
| 4,225,460 A | * | 9/1980 | Newell | ................ 252/429 R |
| 4,503,161 A | * | 3/1985 | Korbel et al. | ............... 502/159 |
| 5,053,277 A | * | 10/1991 | Vassiliades | .............. 428/402.2 |

* cited by examiner

Primary Examiner—Mark L. Bell
Assistant Examiner—Patricia L. Hailey
(74) Attorney, Agent, or Firm—Wenderoth, Lind & Ponack, L.L.P.

(57) ABSTRACT

The invention provides a microencapsulated Lewis acid characterized in that a Lewis acid is supported through coordinate bonds on microcapsules formed of an organic polymer as a novel Lewis acid supported on a polymer in order to overcome the technical limit of conventional catalysts supported on polymers and in addition, to solve problems attendant upon the preparation of a reaction system and separation and recovery from reaction products about Lewis acid catalysts having great industrial usefulness.

8 Claims, 1 Drawing Sheet

MICROENCAPSULATED LEWIS ACID

FIELD OF THE INVENTION

The present invention relates to a microencapsulated Lewis acid where a Lewis acid is confined in a network of a polymer gel. The microencapsulated Lewis acid is in a condition where a Lewis acid is fixed on the surface or the inside of a polymer capsule and confined in certain room to function as a catalyst of organic syntheses.

BACKGROUND OF THE INVENTION

The development of catalysts supported on organic polymers has hitherto been a very important theme of organic syntheses. The reason for this is that the catalysts supported on organic polymers are very economical in view of the preparation and the separation from reaction products and the industrial application thereof is expected. Furthermore, although some of catalysts supported on polymers have been reported so far, the activity of such catalysts is low as compared with carrier-free catalyst and highly active catalysts supported on organic polymers has been very difficult to realize.

On the other hand, attention is directed to Lewis acids because of the characteristic catalytic activity and selectivity of reactions thereof and in addition, the Lewis acids promote catalytic reactions under molder conditions, thus the Lewis acids being recognized to be industrially very useful. However, the Lewis acids decompose in aqueous solutions and are difficult to recover and recycle, and these facts are common to Lewis acid catalysts supported on polymers. For example, although an aluminum chloride catalyst supported on a crosslinked organic polymer is known and can be easily recovered from the reaction system after using once, the catalyst is difficult to recover from the reaction system after using twice or more to make the recycling thereof impossible.

Thus, the conventional Lewis acid catalysts are not necessarily easy in the preparation of reaction systems, the separation from reaction products, and the recovery and recycling thereof. The catalysts supported on organic polymers also are difficult to recover and recycle to make the use thereof uneconomic.

The invention, accordingly, aims at overcoming the technical limit of the conventional catalysts supported on polymers and in addition, at solving problems attendant upon the preparation of reaction systems, the separation from reaction products, and the recovery as to the Lewis acid catalysts having great industrial usefulness, thus to provide novel microencapsulated Lewis acids supported on polymers and catalysts formed of these.

SUMMARY OF THE INVENTION

The invention provides as the first invention a microencapsulated Lewis acid characterized in that s Lewis acid is supported through coordinate bonds on a microcapsule formed of an organic polymer.

In relation to the first invention, the invention also provides a microencapsulated Lewis acid as particles or aggregates thereof as the second invention; a microencapsulated Lewis acid where the organic polymer is a substantially non-crosslinked polymer prepared by addition polymerization as the third invention; a microencapsulated Lewis acid where the organic polymer is a substantially non-crosslinked polymer containing aromatic rings as the fourth invention; a microencapsulated Lewis acid where the organic polymer is a substantially non-crosslinked polymer containing benzene rings as the fifth invention; a microencapsulated Lewis acid where the organic polymer is a substantially non-crosslinked polymer containing aromatic rings on the side chains as the sixth invention; a microencapsulated Lewis acid where the organic polymer is a substantially non-crosslinked polymer containing benzene rings on the side chains as the seventh invention; and a microencapsulated Lewis acid where the Lewis acid is trifluoromethanesulfonate of a rare earth metal as the eighth invention.

The invention further provides as the ninth invention Lewis acid catalysts that are characterized by being formed of the aforesaid microencapsulated Lewis acids of the first through eighth inventions.

Furthermore, the invention provides as the tenth invention a process for preparing a microencapsulated Lewis acid characterized in that a Lewis acid is supported through coordinate bonds on microcapsules simultaneously on forming the microcapsules from an organic polymer by a microencapsulation process and as the eleventh invention a process of preparing the microencapsulated Lewis acid wherein the microencapsulation process is a phase separation process.

In the microencapsulated Lewis acid supported through coordinate bonds on an organic polymer according to the invention, the Lewis acid is arranged on the surfaces of capsules and exposed on the polymer in a condition where the acid is confined and enveloped in complicated room of the inside of capsules, thus to participate in reactions as a catalyst.

DETAILED DESCRIPTION OF THE INVENTION

Description of the Preferred Embodiments

Figure 1:
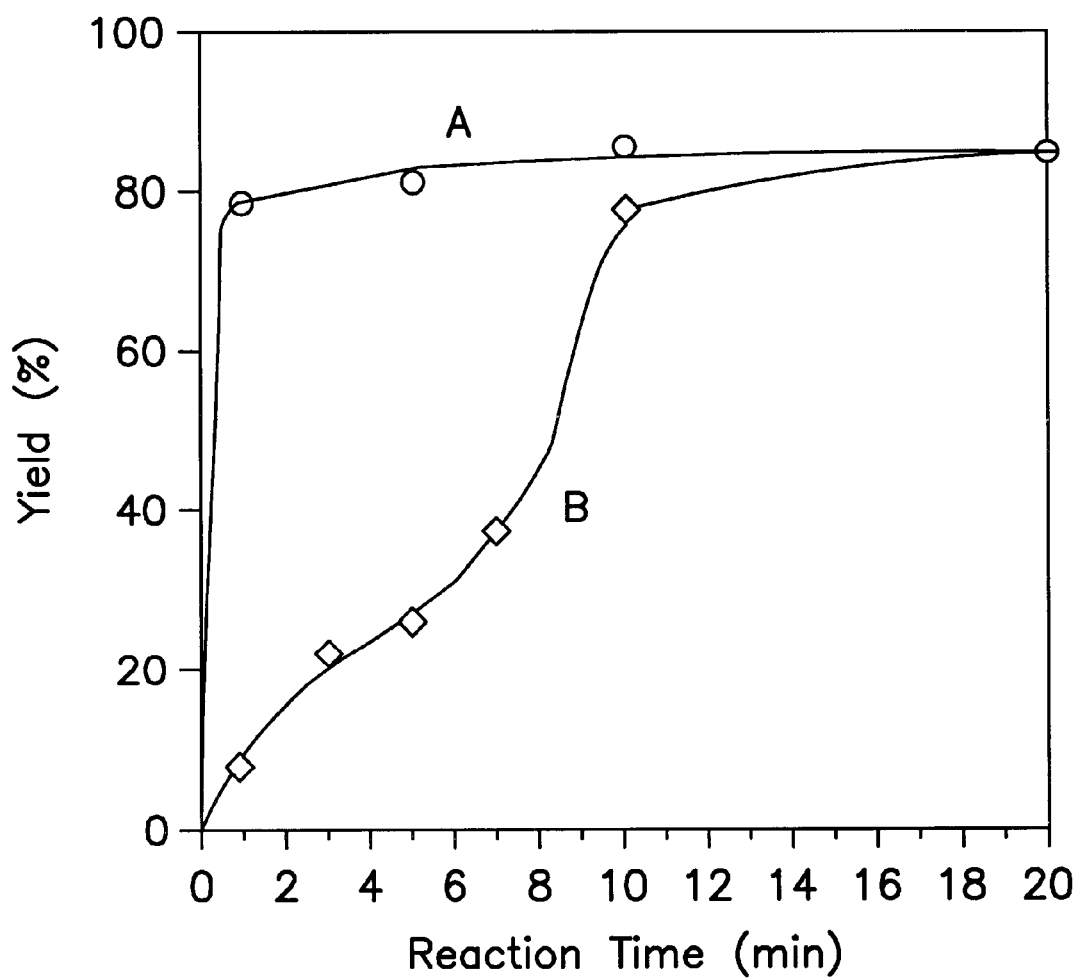
FIG. 1 is a figure showing comparison of reaction activity in Example 15.

The invention possesses the characteristics as described above. Next, the embodiments are illustrated below.

Some examples of the Lewis acids supported on polymers have been reported so far (Neckers, D. C., et al., *J. Am. Chem. Soc.*, 94, 9284 (1972); Drago, R. S., et al., *J. Am. Chem. Soc.*, 110, 3311 (1988); Clark, J. H., et al., *J. Chem. Soc. Chem. Commun.*, 1995, 2037; and others). Furthermore, the present inventors also report some examples (Kobayashi, S., et al., *J. Org. Chem.*, 61, 2256 (1996); and Kobayashi, S., et al., *J. Am. Chem. Soc.*, 118, 8977 (1996)).

These Lewis acids supported on polymers, however, have a disadvantage of having only low catalytic activity as compared with the carrier-free Lewis acids.

Microcapsules formed of organic polymers also are described in Japanese Patent Laid-Open No. 296855/1994. However, the microcapsules have bursting properties to make the recycle thereof impossible and house Lewis acids just physically.

On the other hand, the microencapsulated Lewis acids where Lewis acids are supported through coordinate bonds on organic polymers as described above are easy in the preparation and adjustment thereof, surprisingly exhibit high catalytic activity, can be separated and recovered from reaction products for recycling, and can be used for a variety of organic synthetic reactions. These microencapsulated Lewis acids are substantially different from conventional organic polymer-supported Lewis acids.

Microcapsules formed of organic polymers have hitherto been known in the field of pharmaceuticals. The invention presents for the first time the microencapsulation of Lewis acids and utilization thereof to catalysts.

The microencapsulated Lewis acids of the invention can be provided as fine particles or aggregates having particle sizes of micrometer to nanometer orders. A Lewis acid is supported through coordinate bonds on an organic polymer forming capsules and arranged on the surfaces of the particles or aggregates thereof or exposed and arranged on the polymer in a condition where the Lewis acid is confined and enveloped in complicated room of the insides of the capsules. In the aggregates, the Lewis acid enveloped is found to be exposed also in a condition of the particles contacting with one another. In these conditions, the Lewis acid acts and exhibits stable action and further higher catalytic activity as compared with the carrier-free Lewis acid.

Both crosslinked and non-crosslinked organic polymers can be used as the organic polymers as long as the polymers can undergo microencapsulation, but substantially non-crosslinked polymers are preferred. Polymers formed by addition polymerization are more appropriate. More concretely, the polymers are substantially non-crosslinked polymers containing aromatic rings, desirably benzene rings, including polystyrene, styrene/acrylonitrile copolymers, and styrene/MMA copolymers.

In the Lewis acid supported through coordinate bonds on microcapsules formed of an organic polymer containing benzene rings, it is through that the mutual interaction between the Lewis acid and $\pi$-electrons of the benzene rings causes effective catalytic action.

The substantially non-crosslinked polymers means polymers that are not subjected to crosslinking reaction by use of crosslinking agents, which does not mean to exclude polymers where a small number of crosslinking structures are produced in the course of preparation of the polymers. That is, the polymers need to contain substantially no crosslinked polymer gel unnecessary to solvents.

In the organic polymers containing aromatic rings, the aromatic rings in molecular structure can be those forming the main chain of the polymer or those existing in the side chains. From the viewpoint of the mutual interaction by coordinate bonds between a Lewis acid and $\pi$-electrons of a benzene ring, for example, in the case of polystyrene or copolymers or block copolymers of styrene and another monomer, organic polymers that are formed by addition polymerization and contain benzene rings on the side chains are more preferred.

The organic polymers containing aromatic rings can have a variety of molecular structures such as a polyolefin structure, a polyester structure, a polyether structure, and a polyamide structure as long as the polymers contain aromatic rings in structures. Or copolymers of various monomers can also be included therein. Although the molecular weight thereof is not particularly limited, polymers having a weight average molecular weight of about 10,000 to about 2,000,000 are usable in general.

Supporting of the Lewis acids on microcapsules formed of these organic polymers can be carried out by various methods. Interfacial polymerization, phase separation (coacervation), and interfacial precipitation are known as simple methods. In the invention, the phase separation (coacervation) is preferably applied.

Lewis acids forming the microencapsulated Lewis acid of the invention are those defined as electron-pair acceptors and a variety of Lewis acids are usable. Although known Lewis acids such $AlCl_3$ or $BF_3$ can also be used, examples of Lewis acids used preferably in the invention include organic metallic compounds of rare earth metals of scandium (Sc), yttrium (Y), and lanthanide (Ln) series, for example, trifluoromethanesulfonates of rare earth metals such as scandium trifluoromethanesulfonate (scandium triflate), yttrium triflate, and lanthanide triflates (Ln=La, Ce, Pr, Nd, Sm, Eu, Gd, Tb, Dy, Ho, Er, Tm, Yb, and Lu). Above all, scandium compounds that the present inventors have found are stable in an aqueous phase and preferably exemplified. Of these, a typical Lewis acid is scandium triflate $[Sc(OTf)_3]$.

The amount of a Lewis acid supported on microcapsules formed of an organic polymer is not particularly limited and can be selected depending upon a Lewis acid used, an organic polymer used, the purpose of use of a microencapsulated Lewis acid adopted, and a use. For example, when the aforesaid polymers having a weight average molecular weight of about 10,000 to about 2,000,000 are used, the weight ratio of a Lewis acid to an organic polymer in general is 1:100 or more, and preferably from 1:3 or less to 1:50 or more as a standard.

In the invention, the microencapsulated Lewis acids as described above are used as catalysts for a variety of organic synthetic reactions.

The microencapsulated Lewis acids can be used as catalysts in both embodiments of a batchwise reaction system and a flow reaction system, for example, for a variety of organic synthetic reactions such as imino-aldol condensation, Mannich-type reaction, aldol reaction, Michael reaction, and Friedel-Crafts reaction. In addition, the catalysts of the invention are found to have high reaction activity and to bring about high reaction yields (selectivity) as compared with single carrier-free Lewis acids. A very significant action where the microencapsulated Lewis acids recovered from reaction mixtures also exhibit high reaction activity on recycling is confirmed.

Of course, when the microencapsulated Lewis acids are recovered by separation from reaction products, the recovery as a solid (particles) can be very easily carried out.

EXAMPLES

The embodiments of the invention are illustrated in further detail through the following examples, but these are not to be construed as limiting the invention.

Example 1

A microencapsulated Lewis acid of the invention was prepared according to the following procedure. A Phase separation (coacervation) microencapsulation process was adopted in this procedure.

First, 1.000 gram of polystyrene having a weight average molecular weight of 280,000 was dissolved in 20 ml of cyclohexane at a temperature of 40° C. and subsequently, 0.200 gram of scandium triflate $[Sc(OTf)_3]$ was added to the resulting solution.

The resulting mixture separated was stirred at the aforesaid temperature for 1 hour and gradually cooled to 0° C. Phase separation (coacervation) arose to form a condition of covering scandium triflate with polystyrene. Thirty ml of hexane was added thereto to harden particle walls of microcapsules.

After further stirring for 1 hour, a microcapsule particle product was washed with acetonitrile several times and then dried at 50° C.

Since 0.08 gram of scandium triflate was recovered in the procedure described above, it was confirmed that 0.120 gram of scandium triflate was supported on the microcapsules.

The total weight of the microencapsulated Lewis acid was 1.167 grams (acetonitrile was contained).

The IR absorption spectrum (KBr) thereof is shown in the following Table 1.

TABLE 1

The weight of the capsules was 1.167 g which contained acetonitrile.
IR (KBr) 3062, 3030 (vCH), 1946, 1873, 1805 (δCH), 1601, 1493 (benzene rings). 1255 ($v_{25}SO_2$), 1029 ($v_9SO_2$), 756 (vC-S). 696 (vS-O) $cm^{-1}$. Cf. $Sc(OTf)_3$: 1259 ($vSO_2$); 1032 ($vSO_2$), 769 (vC-S), 647 (vS-O) $cm^{-1}$; polystylene: 3062, 3026 (vCH, 1944, 1873, 1803 (δCH), 1600, 1491 (benzene rings) $cm^{-1}$.

On the basis of a scanning electron microscope (SEM) and a scandium energy dispersion X-ray (EDX) map, a microcapsule structure was unable to be identified in the strict sense. It was confirmed, however, that fine particles were in tightly collective condition and scandium triflate was arranged on the surfaces of polymer microcapsules.

Example 2

The microencapsulated Lewis acid prepared in Example 1 was used as a catalyst and an imino-aldol reaction was carried out as shown in Table 2.

The reaction was carried out by use of the microcapsule particle product containing 0.120 gram of scandium triflate [MC $Sc(OTf)_3$] by a flow process through a circulating column in acetonitrile solvent at room temperature for 3 hours.

That is, 1.167 grams of the aforesaid [MC $Sc(OTf)_3$] as a catalyst was placed in a column (1.6×15 cm) and 10 ml of acetonitrile was added thereto. A mixture of 0.50 mmol of aldimine and 0.60 mmol of silyl enolate in 5 ml of acetone was added and the solution was circulated at room temperature for 3 hours.

The solution was recovered and concentrated under vacuum. The resulting crude product was purified by chromatography on silica gel.

The microencapsulated Lewis acid [MC $Sc(OTf)_3$] was recovered and recycled to use seven times.

The yields of reactions also are contained in Table 2.

TABLE 2

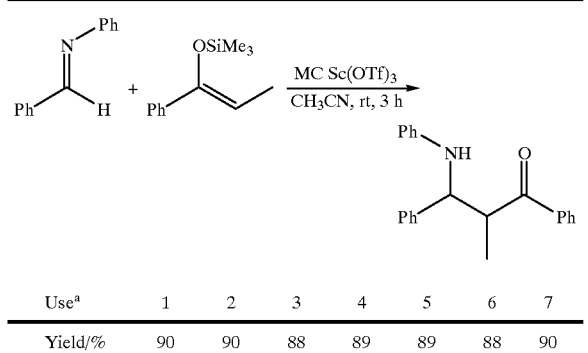

| Use[a] | 1 | 2 | 3 | 4 | 5 | 6 | 7 |
|---|---|---|---|---|---|---|---|
| Yield/% | 90 | 90 | 88 | 89 | 89 | 88 | 90 |

[a]Recovered catalyst was used successively (Use 2, 3, 4, . . .)

It was confirmed that the aminocarbonyl compound as a reaction product was prepared in very high yields and further, recycling of the catalyst caused no reduction in yields.

This shows that the catalyst of the invention exerts an extremely significant action beyond expectation.

Example 3

Similarly to Example 2, a Mannich type reaction was carried out wherein three starting materials were used as shown in Table 3.

Similarly to Example 2, high yields were obtained as shown in Table 3. In addition, it also was confirmed that recycling of the catalyst caused no reduction in yield.

TABLE 3

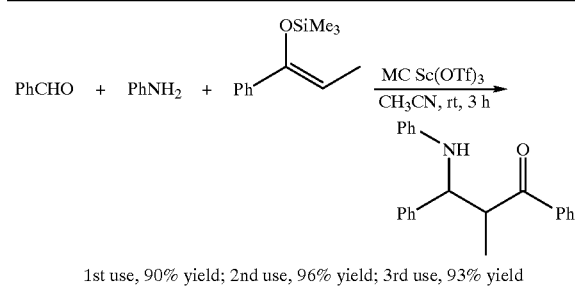

1st use, 90% yield; 2nd use, 96% yield; 3rd use, 93% yield

Example 4

The microencapsulated Lewis acid [MC $Sc(OTf)_3$] prepared in Example 1 was used as a catalyst and an aldol reaction was carried out in a batchwise system as shown in Table 4. The reaction time was 6 hours.

Table 4 reveals that a hydroxycarbonyl compound was prepared in yields higher than 90 percent and an extremely high yield of 95 percent was maintained even after the catalyst was used three times through recycling.

TABLE 4

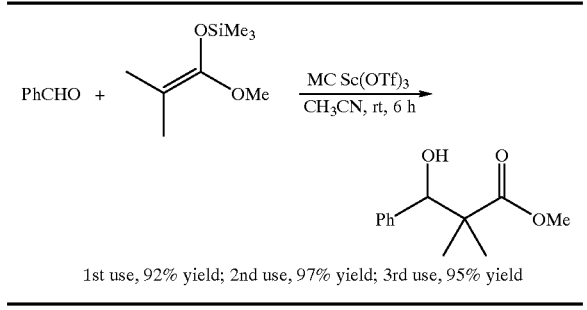

1st use, 92% yield; 2nd use, 97% yield; 3rd use, 95% yield

Example 5

Similarly to Example 4, a Michael reaction was carried out according to a batchwise system as shown in Table 5.

It was confirmed that use of the microencapsulated Lewis acid catalyst of the invention makes it possible to maintain a high reaction yield in spite of recycling of the catalyst as shown in Table 5.

TABLE 5

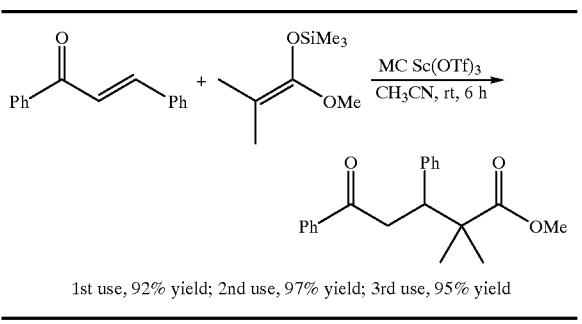

1st use, 92% yield; 2nd use, 97% yield; 3rd use, 95% yield

Example 6

Similarly to Example 4, a Friedel-Crafts acylation reaction was carried out as shown in Table 6.

The reaction was carried out in nitromethane in the coexistence of LiClO$_4$ at a temperature of 50° C. for 6 hours.

It was confirmed that a yield of 81 percent was obtained even after the catalyst was used three times through recycling and a high level of yield was maintained as shown in Table 6.

TABLE 6

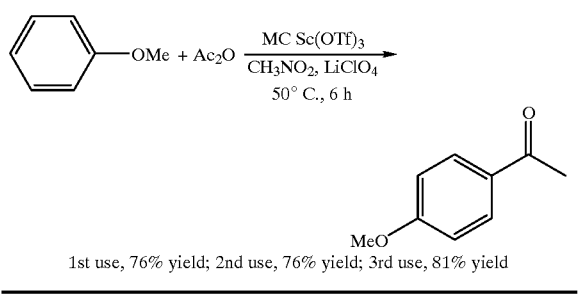

1st use, 76% yield; 2nd use, 76% yield; 3rd use, 81% yield

Example 7

An allylation reaction of an aldehyde was carried out as shown in Table 7. The reaction was carried out by a batchwise system according to the following procedure.

That is, 1.167 grams of the microencapsulated Lewis acid containing 0.120 gram of scandium triflate [MC Sc(OTf)$_3$] prepared in Example 1 was used as a catalyst and a mixture of 0.50 mmol of an aldehyde and 0.30 mmol of tetraallyl tin in 5 ml of acetonitrile was mixed with the catalyst at room temperature.

The resulting mixture was stirred at the same temperature for 2 hours. After filtration, the filtrate was concentrated under vacuum and the resulting crude product was purified by chromatography on silica gel.

The catalyst was used three times through recycling.

The yields of reactions were shown in Table 7.

TABLE 7

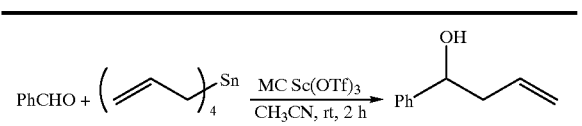

| Use* | Yield/% |
|---|---|
| 1 | 92 |
| 2 | 91 |
| 3 | 90 |

It was confirmed that a yield higher than 90 percent was maintained in spite of repeated recycling.

Example 8

Similarly to Example 7, a cyanidation reaction of an aldehyde was carried out as shown in Table 8.

It was confirmed that the catalyst of the invention maintained a high yield in spite of recycling.

TABLE 8

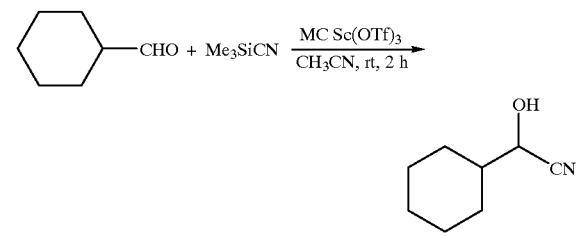

| Use | Yield/% |
|---|---|
| 1 | 79 |
| 2 | 78 |
| 3 | 74 |

Example 9

Similarly to Example 7, a Diels-Alder reaction was carried out as shown in Table 9.

The catalyst supported on a polymer of the invention was found to have excellent catalytic activity and to exhibit maintenance of the high activity in recycling.

TABLE 9

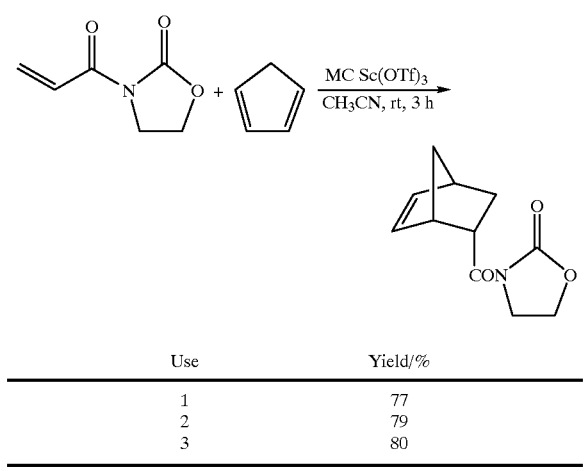

| Use | Yield/% |
|---|---|
| 1 | 77 |
| 2 | 79 |
| 3 | 80 |

Example 10

Similarly to Example 2, an Aza Diels-Alder reaction was carried out as shown in Table 10.

Recycling of the catalyst was found to maintain a high yield.

TABLE 10

[Reaction scheme: N-Ph imine + furan derivative, MC Sc(OTf)₃, CH₃CN, rt, 4 h → tetracyclic product]

| Use | Yield/% |
|---|---|
| 1 | 80 |
| 2 | 78 |
| 3 | 78 |

Example 11

Similarly to Example 2, a cyanidation reaction was carried out as shown in Table 11.

Recycling of the catalyst was found to maintain high yields of the same level as that in use of the virgin catalyst.

TABLE 11

[Reaction scheme: PhCH=NPh + Me₃SiCN, MC Sc(OTf)₃, CH₃CN, rt, 4 h → Ph-CH(NHPh)-CN]

| Use | Yield % |
|---|---|
| 1 | 77 |
| 2 | 77 |
| 3 | 76 |

Example 12

Similarly to Example 11, a cyanidation reaction was carried out wherein three starting materials were used as shown in Table 12.

Recycling of the catalyst gave yields higher than that in use of the virgin catalyst.

TABLE 12

[Reaction scheme: PhCHO + PhNH₂ + Me₃SiCN, MC Sc(OTf)₃, CH₃CN, rt, 4 h → Ph-CH(NHPh)-CN]

| Use | Yield/% |
|---|---|
| 1 | 70 |
| 2 | 71 |
| 3 | 75 |

Example 13

Similarly to Example 2, an allylation reaction was carried out as shown in Table 13.

It was confirmed that the catalyst was able to maintain high reaction yields in spite of recycling.

TABLE 13

[Reaction scheme: PhCH=NPh + (allyl)₄Sn, MC Sc(OTf)₃, CH₃CN, rt, 2 h → Ph-CH(NHPh)-CH₂CH=CH₂]

| Use[a] | Yield/% |
|---|---|
| 1 | 85 |
| 2 | 87 |
| 3 | 83 |

Example 14

Similarly to Example 2, Quinoline synthesis was carried out as shown in Table 14.

It was confirmed that the catalyst was able to maintain high reaction yields in spite of recycling.

TABLE 14

[Reaction scheme: PhCHO + PhNH₂ + furan, MC Sc(OTf)₃, CH₃CN, rt, 4 h → tetracyclic product]

| Use | Yield/% |
|---|---|
| 1 | 68 |
| 2 | 69 |
| 3 | 59 |

Example 15

In the imino-aldol reaction of Example 2, catalytic activity was compared about the microencapsulated Lewis acid [MC Sc(OTf)₃] of the invention and the carrier-free catalyst Sc(OTf)₃.

The amounts of Sc(OTf)₃ in the respective catalysts were identically 0.120 gram.

The relationship between reaction times and yields is shown in FIG. 1. FIG. 1 reveals that the catalyst of the invention (A in the FIGURE) has high reaction activity and allows the imino-aldol reaction to proceed much more rapidly as compared with the carrier-free catalyst Sc(OTf)₃ (B in the FIGURE).

As described in detail, in the invention, Lewis acids useful as catalysts for a variety of organic synthetic reactions are supported through coordinate bonds on polymers to exerts a very significant action that the preparation, recovery, and recycling thereof are easy, the activity as a catalyst is high and the high activity is maintained also in recycling.

What is claimed is:

1. A microencapsulated Lewis acid characterized in that a Lewis acid is supported through coordinate bonds on microcapsules formed of a substantially non-crosslinked polymer formed by addition polymerization.

2. The microencapsulated Lewis acid of claim 1 wherein the substantially non-crosslinked polymer contains aromatic rings.

3. The microencapsulated Lewis acid of claim 2 wherein the substantially non-crosslinked polymer contains benzene rings.

4. The microencapsulated Lewis acid of any one of claims 1–3 wherein the Lewis acid is a trifluoromethanesulfonate of a rare earth metal.

5. A Lewis acid supported through coordinate bonds on a substantially non-crosslinked polymer which contains aromatic rings on side chains.

6. The Lewis acid supported on a polymer of claim 5 wherein the substantially non-crosslinked polymer contains benzene rings on the side chains.

7. The Lewis acid supported on a polymer of claim 5 or 6 wherein the Lewis acid is a trifluoromethanesulfonate of a rare earth metal.

8. A process for preparing a microencapsulated Lewis acid which comprises supporting a Lewis acid through coordinate bonds on microcapsules on formation of the microcapsules from substantially non-crosslinked polymer by a microencapsulation process.

\* \* \* \* \*